United States Patent [19]

Mongelli et al.

[11] Patent Number: 5,420,296
[45] Date of Patent: May 30, 1995

[54] NEW UREIDO DERIVATIVES OF POLY-4-AMINO-2-CARBOXY-1-METHYL COMPOUNDS

[75] Inventors: Nicola Mongelli, Milan; Giovanni Biasoli, Gavirate; Alfredo Paio, Cernusco sur Naviglio (Milan); Maria Grandi, Reggio Emilia; Marina Ciomei, Torre d'Isola, all of Italy

[73] Assignee: Farmitalia Carlo Erba S r l, Milan, Italy

[21] Appl. No.: 66,583

[22] Filed: May 25, 1993

Related U.S. Application Data

[62] Division of Ser. No. 752,577, Sep. 9, 1991, Pat. No. 5,260,329.

[30] Foreign Application Priority Data

Jan. 11, 1990 [GB] United Kingdom .................. 9000644

[51] Int. Cl.⁶ ............................................. C07D 207/34
[52] U.S. Cl. ..................................... 548/518; 530/331; 548/530; 548/532
[58] Field of Search ......................... 548/530, 532, 518; 530/331

[56] References Cited

U.S. PATENT DOCUMENTS 2,785,182  3/1957  Walle ................................... 548/518
2,785,183  3/1957  Waller .................................. 548/518

FOREIGN PATENT DOCUMENTS

72210/74  2/1976  Australia .

OTHER PUBLICATIONS

European Office Action in Corresponding European Application No. 91 902 204.6, Dated Jul. 4, 1994.

Chemical Abstracts, vol. 68, p. 2086 (1968), No. 21767z.
Chemical Abstracts, vol. 68, p. 8391 (1968), No. 87088k.

*Primary Examiner*—Robert Gerstl
*Attorney, Agent, or Firm*—Oblon, Spivak, McClelland, Maier & Neustadt

[57] ABSTRACT

The invention relates to ureido derivatives of substituted pyrroles of formula

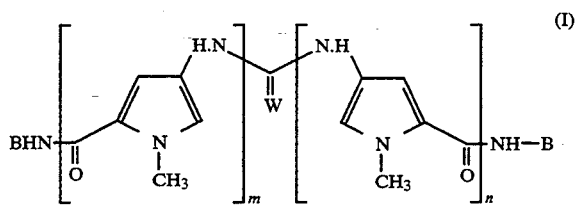

wherein each of m and n, being the same, is an integer of 1 to 3;
W is oxygen of sulphur;
each of the B groups, which are the same, is
a) a saturated or unsaturated, carbocyclic or condensed carbocyclic ring substituted by one or more acid groups;
b) a saturated or unsaturated, heteromonocyclic or heterobicyclic ring, containing one or more heteroatoms chosen from nitrogen, oxygen and sulphur, substituted by one or more acid groups;
c) a pyranyl or furanyl sugar residue substituted by one or more acid groups; or
d) a —CH$_2$(CHA)$_r$CH$_2$A group, wherein each A group, being the same or different, is an acid group and r is 0, 1 or 2; and the pharmaceutically acceptable salts thereof, which are useful as angiogenesis inhibitors.

2 Claims, No Drawings

NEW UREIDO DERIVATIVES OF POLY-4-AMINO-2-CARBOXY-1-METHYL COMPOUNDS

This application is a Divisional of application Ser. No. 07/752,577, filed Sep. 9, 1991, U.S. Pat. No. 5,260,329, which was filed as International Application No. PCT/EP91/00014 on Jan. 7, 1991.

The present invention relates to ureido derivatives of substituted pyrroles, to a process for their preparation and to a pharmacological composition containing them. The pyrrole derivatives of the invention may be regarded as derivatives of Distamycin A which is a known compound having the following formula

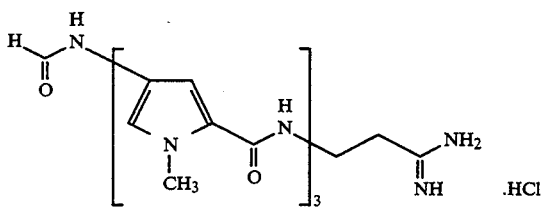

Literature referring to Distamycin A includes, for example NATURE 203, 1064 (1964).

The present invention provides ureido derivatives of substituted carboxypyrroles having the following general formula (I)

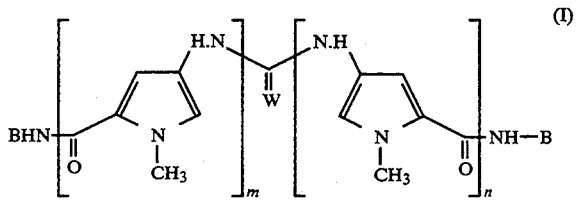

wherein
each of m and n, being the same, is an integer of 1 to 3; W is oxygen of sulphur;
each of the B groups, which are the same, is a) a saturated or unsaturated, carbocyclic or condensed carbocyclic ring substituted by one or more acid groups;

b) a saturated or unsaturated, heteromonocyclic or heterobicyclic ring, containing one or more heteroatoms chosen from nitrogen, oxygen and sulphur, substituted by one or more acid groups;

c) a pyranyl or furanyl sugar residue substituted by one or more acid groups; or d) a —CH$_2$(CHA)$_r$CH$_2$A group, wherein each A group, being the same or different, is an acid group and r is 0, 1 or 2; and the pharmaceutically acceptable salts thereof.

When two or more acid groups are present on a B group, as defined above under a), b) and c), they may be the same or different. Examples of acid groups according to the definition of a B group given above under a), b), c) and d) for instance may be those chosen from the group including sulfonic, sulfuric, sulfamic, sulfinic, phosphoric, phosphonic, phosphamic or carboxylic acid groups, i.e. SO$_3$H, SO$_4$H, SO$_3$NH$_2$, SO$_2$H, PO$_4$H$_2$, PO$_3$H$_2$, PO$_3$NH$_3$ and CO$_2$H.

Preferably the B groups, as defined above under a), b) and c), are substituted by 1 to 3 of such acid groups.

When B is a ring as defined above under a) it is for example phenyl or naphthyl. When B is a ring as defined above under b) it is for example tetrahydropyranyl or tetrahydrofuranyl. When B is a sugar residue as defined above under c) it is for example a residue deriving from glucose or ribose.

When B is a group as defined above under d) r is preferably 2.

As already said, the invention includes within its scope also the pharmaceutically acceptable salts of the compounds of formula (I).

Examples of pharmaceutically acceptable salts are either those with inorganic bases, such as sodium, potassium, calcium and aluminium hydroxydes, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines.

Preferred compounds according to the present invention are the compounds of formula (I), wherein
each of m and n, being the same, is 2;
W is oxygen;
each of the B groups, which are the same, is a') an unsaturated carbocyclic or condensed carbocyclic ring substituted by 1 to 3 acid groups; b') a tetrahydropyranyl or tetrahydrofuranyl ring substituted by 1 to 3 acid groups; or c') a glucosefuranosyl residue substituted by 1 to 3 acid groups; and the pharmaceutically acceptable salts thereof.

Specific examples of preferred compounds of the invention, are the followings:

8,8'-(carbonyl-bis(imino-N-methyl-4,2-pyrrolecarbonyl-imino(N-methyl-4,2-pyrrole)carbonylamino))-bis(1,3-naphthalendisulfonic acid);

8,8'-(carbonyl-bis(imino-N-methyl-4,2-pyrrolecarbonyl-imino(N-methyl-4,2-pyrrole)carbonylimino))-bis(3,5-naphthalendisulfonic acid);

8,8'-(carbonyl-bis(imino-N-methyl-4,2-pyrrolecarbonyl-imino(N-methyl-4,2-pyrrole)carbonylimino))-bis(2,5 -naphthalendisulfonic acid);

8,8'-(carbonyl-bis(imino-N-methyl-4,2-pyrrolecarbonyl-imino(N-methyl-4,2-pyrrole)carbonylimino))-bis(2,4-naphthalendisulfonic acid);

8,8'-(carbonyl-bis(imino-N-methyl-4,2-pyrrolecarbonyl-imino(N-methyl-4,2-pyrrole)carbonylimino))-bis(1,6-naphthalendisulfonic acid);

8,8'-(carbonyl-bis(imino-N-methyl-4,2-pyrrolecarbonyl-imino(N-methyl-4,2-pyrrole)carbonylimino))-bis(2,6-napthalendisulfonic acid);

8,8'-(carbonyl-bis(imino-N-methyl-4,2-pyrrolecarbonyl-imino(N-methyl-4,2-pyrrole)carbonylimino))-bis(3,6-naphthalendisulfonic acid);

8,8'-(carbonyl-bis(imino-N-methyl-4,2-pyrrolecarbonyl-imino(N-methyl-4,2-pyrrole)carbonylimino))bis(1,5-naphthalendisulfonic acid);

8,8'-(carbonyl-bis(imino-N-methyl-4,2-pyrrolecarbonyl-imino(N-methyl-4,2-pyrrole)carbonylimino))-bis(1-naphthalensulfonic acid);

8,8'-(carbonyl-bis(imino-N-methyl-4,2-pyrrolecarbonyl-imino(N-methyl-4,2-pyrrole)carbonylimino))bis(3-naphthalensulfonic acid);

8,8'-(carbonyl-bis(imino-N-methyl-4,2-pyrrolecarbonyl-imino(N-methyl-4,2-pyrrole)carbonylimino))-bis(5-naphthalensulfonic acid);

8,8'-(carbonyl-bis(imino-N-methyl-4,2-pyrrolecarbonyl-imino(N-methyl-4,2-pyrrole)carbonylimino))-bis(1,3,5-naphthalentrisulfonic acid);

8,8'-(carbonyl-bis(imino-N-methyl-4,2-pyrrolecarbonyl-imino(N-methyl-4,2-pyrrole)carbonylimino))-bis(1,4,6-naphthalentrisulfonic acid);

8,8'-(carbonyl-bis(imino-N-methyl-4,2-pyrrolecarbonyl-imino(N-methyl-4,2-pyrrole)carbonylimino))-bis(2,4,6-naphthalentrisulfonic acid);

8,8'-(carbonyl-bis(imino-N-methyl-4,2-pyrrolecarbonyl-imino(N-methyl-4,2-pyrrole)carbonylimino))-bis(1,3,6-naphthalentrisulfonic acid);

8,8'-(carbonyl-bis(imino-N-methyl-4,2-pyrrolecarbonyl-imino(N-methyl-4,2-pyrrole)carbonylimino))-bis(2,3,5-naphthalensulfonic acid);

2,2'-(carbonyl-bis(imino-N-methyl-4,2-pyrrolecarbonyl-imino(N-methyl-4,2-pirrole)carbonylimino))-bis(2-deoxy-D-glucose-6-sulphate); and 2,2'(carbonyl-bis(imino-N-methyl-4,2-pyrrolecarbonyl-imino(N-methyl-4,2-pyrrole)carbonylimino))bis(2-deoxy-D-glucose-6-phosphate);

and the pharmaceutically acceptable salts thereof, in particular the sodium and potassium salts.

The compounds of the invention, and the salts thereof, can be prepared by a process comprising reacting a compound of formula (II)

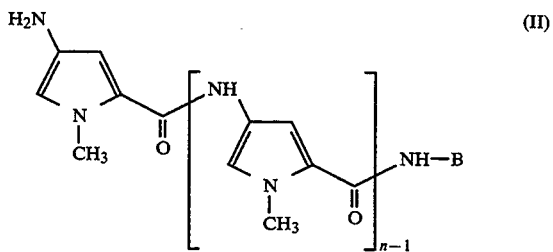

(II)

wherein n and B are as defined above, or a salt thereof, with a compound of formula (III)

(III)

wherein W is as defined above, and each of the X groups, which may be the same or different, is a good leaving group, and if desired, salifying a compound of formula (I) thus obtained; and/or if desired, obtaining a free compound of formula (I) from a salt thereof.

A salt of a compound of formula (II) may be a salt with inorganic bases, for example those mentioned above as to the pharmaceutically acceptable salts of the invention, the sodium and potassium salts being the preferred.

Preferred examples of good leaving groups, according to the meaning of X, are halogen atoms, in particular chlorine, or other easily displaceable groups such as, imidazolyl, triazolyl, p-nitrophenoxy or trichlorophenoxy.

The reaction of a compound of formula (II), or a salt thereof, with a compound of formula (III) is an analogy process and can be carried out according to well known methods; for example according to the conditions described in organic chemistry for this kind of reaction, i.e. for synthesis of urea derivatives. Preferably when in a compound of formula (III) X is an halogen atom, e.g. chlorine, the reaction may be carried out at a molar ratio of compound (II), or a salt thereof: compound (III) from about 1:1 to about 1:4. The reaction is preferably performed in organic solvents such as dimethylsulphoxide, hexamethylphosphotriamide, dimethylacetamide or, preferably, dimethylformamide, or their aqueous mixtures, or in water/dioxane or water/toluene mixtures, in the presence of either an organic base such as triethylamine or diisopropylethylamine, or an inorganic base such as sodium bicarbonate or sodium acetate. The reaction temperature may vary from about −10° C. to about 50° C. and the reaction time from about 1 to about 12 hours.

The compounds of formula (I) prepared according to the above described procedures may be purified by conventional methods such as by silica gel or alumina column chromatography, and/or by rechrystallization from organic solvents such as lower aliphatic alcohols or dimethylformamide.

Analogously salification of a compound of formula (I) can be carried out by known methods in the art.

The compounds of formula (II) may be obtained according to known procedures.

For instance, a compound of formula (II) may be obtained by reduction of a compound of formula (IV)

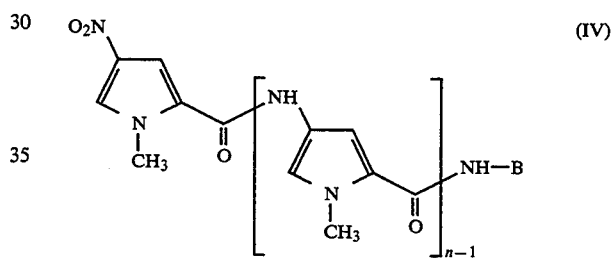

(IV)

wherein n and B are as defined above by methods well known in the art. The compounds of formula (IV) may be obtained by reacting an amine of formula B—NH$_2$, where B is defined as above, with a compound of formula (V)

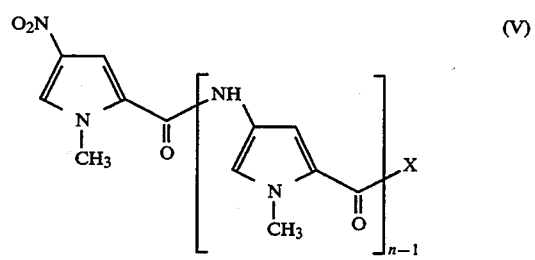

(V)

wherein n and X are as defined above.

Also the reaction of an amine of formula B—NH$_2$ with a compound of formula (V) is a well known process.

Alternatively a compound of formula (IV) wherein n is 2 or 3 may be obtained by a multi-step-process comprising reacting a compound of formula (VI)

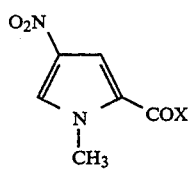

wherein X is as defined above, with an amine of formula B—NH$_2$, in which B is as defined above. The reaction, which may be carried out according to known methods, provides compounds of formula (VII)

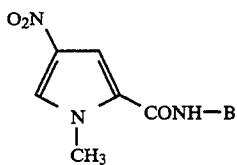

wherein B is as defined above.

A compound of formula (VII) is reduced according to known methods to provide a compound of formula (VIII)

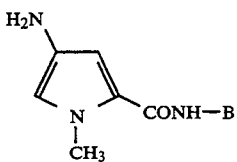

wherein

B is as defined above, wich in its turn is reacted with a compound of formula (VI), as defined above, thus obtaining a compound of formula (IV), as defined above, wherein n is 2. If a compound of formula (IV), wherein n is 3 is desired, a further reduction and acylation step is required.

The compounds of formula (V) are known compounds and may be obtained for example according to Heterocycles, vol 27, No. 8, 1988, p. 1945–52.

The compounds of formula (VI) and the amine of formula B—NH$_2$ are known products or may be easily obtained according to known methods.

PHARMACOLOGY

The compounds of the invention have been found to be active as angiogenesis inhibitors.

Angiogenesis inhibitor is meant an agent capable of suppressing the growth of new blood vessels. Therefore the compounds of the present invention are useful in treating several pathological conditions in mammals, including humans, where the growth of new blood vessels is detrimental, for example in chronic inflammation, diabetic retinopathy, psoriasis, rheumatoid arthritis and tumor growth. In particular, in the cancer therapy the compounds of the invention can be administered alone or in association with antitumor agents such as doxorubicin, etoposide, fluorouracil, mephalan, cyclophosphamide, bleomycin, vinblastin or mitomycin. The angiogenesis inhibitor activity of the compounds of the present invention is shown e.g. by the fact that they have been found to be active in the chorioallantoic membrane test, according to the Folkman's method [Nature, 297, 307 (1982)].

Moreover the compounds of the present invention have been found to be endowed with TNF α-neutralizing activity and therefore they can be employed in humans for prophylactic and/or therapeutic use in any disease state in which TNF α is known to play a detrimental role. Typically such disease states are cachexia, septic shock, graft-versus-host disease, AIDS, cerebral malaria, rheumatoid arthritis. The TNF α-inhibiting activity of the compounds according to the present invention is proven, for instance, by the fact that they are active in inhibiting the cytotoxic activity of human TNFα on untreated mouse LM cells.

The compounds of the invention can be administered by the usual routes, for example, parenterally, e.g. by intravenous injection or infusion, intramuscularly, subcutaneously, topically or orally. The dosage depends on the age, weight and conditions of the patient and on the administration route.

For example, a suitable dosage for administration to adult humans may range from about 0.5 to about 300 mg pro dose 1–4 times a day.

The pharmaceutical compositions of the invention may contain a compound of formula (I) as the active substance, in association with one or more pharmaceutically acceptable excipients and/or carrier The pharmaceutical compositions of the invention are usually prepared following conventional methods and are administered in a pharmaceutically suitable form.

For instance, solutions for intravenous injection or infusion may contain as carrier, for example, sterile water or preferably, they may be in the form of sterile aqueous isotonic saline solutions.

Suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleoginous or emulsifying excipients.

The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates: and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

Furthermore, according to the invention there is provided a method of treating pathological conditions where the growth of new blood vessels is detrimental, for example chronic inflammation, diabetic retinopathy, psoriasis, rheumatoid arthritis and tumors, in mammals in need thereof, including humans, comprising administering to the said mammals a composition of the invention.

Object of the present invention are also products containing a compound of formula (I), or a pharmaceutically acceptable salt thereof, and a biologically active amount of a different active agent, as a combined preparation for simultaneous, separate or sequential use in the treatment of a disease in which TNFα plays a detrimental role. The term "combined" method of treatment is meant to include both separate and substantially contemporaneous administration of a composition containing a therapeutically effective amount of a compound of formula (I), or a pharmaceutically acceptable salt thereof, and a pharmaceutical composition containing a therapeutically effective amount of a different pharmaceutically active agent.

Active agents, that can be formulated with a compound of the invention or alternatively, can be administered in a combined method of treatment depend on the disease state to be cured and are, for instance, gamma globulin, immune globulin and monoclonal antibody products, antibiotics and antimicrobial products. Typically, the antimicrobial agents may include a penicillin in conjunction with an aminoglycoside (e.g. gentamycin, tobramycin). However several well known additional agents, e.g. cephalosporins, can be utilized.

The following examples illustrate but do not limit the invention.

EXAMPLE 1

8,8'-(carbonyl-bis(imino-N-methyl-4,2-pyrrolecarbonyl-imino(N-methyl-4,2-pyrrole)carbonylimino))-bis(1,5-naphthalendisulfonic acid tetrasodium salt.

To a solution of 8-(amino-N-methyl-4,2-pyrrolecarbonyl-imino(N-methyl-4,2-pyrrole)carbonylimino))(1,5-naphthalendisulfonic acid) disodium salt hydrochloride (0.6 g., 1.02 $10^{-3}$ mols) in water (20 ml), sodium acetate (0.328 g., 4 mmols) was added under stirring. The whole was cooled to 0° C. with an ice-salt bath, then a solution of phosgene in toluene (1 ml ~4 eq.) was added dropwise. The mixture was stirred 1 hr at 0° C.

The solvents were evaporated under vacuum and the residue was taken up with methanol and filtered. The filtrate was evaporated and the residue was chromatographed on a silica gel column with methylene chloride:methanol: 60:40 as eluent, affording 0.16 g. of the title compound.

I.R. (KBr) cm$^{-1}$: 3440 b, 1660, 1640, 1585, 1180, 1030.

N.M.R. (DMSO-d6): δ 3.84 (3H,s); 3.85 (3H,s); 6.80 (1H,d); 7.07 (2H,m); 7.41 (2H,m); 7.92 (2H,dd); 8.12 (1H,s); 8.27 (1H,dd); 9.07 (1H,dd); 9.90 (1H,bs); 12.27 (1H,bs).

F.A.B.-M.S.: m/z 1209; M$^+$+1; 1231, M$^+$+23; 1128, M-80 U.V. (H$_2$O) nm: λ max (E$_{1\,cm}$1%): 316 (331), 229 (478).

By analogous procedure the following compounds can be obtained: 8,8'-(carbonyl-bis(imino-N-methyl-4,2-pyrrole-carbonyl-imino(N-methyl-4,2-pyrrole)carbonylimino))bis(3-naphthalensulfonic acid)disodium salt.

I.R. (KBr)cm$^{-1}$: 3430 b, 1640, 1585, 1200, 1030.

N.M.R. (DMSO-d6): δ 3.84 (6H,s); 6.86 (1H,d); 7.05 (1H,d); 7.24 (1H,d); 7.35 (1H,d); 7.54 (2H,m); 7.70 (1H,dd); 7.90 (2H,m); 8.15 (1H,d); 8.15 (1H,d); 8.95 (1H,bs); 9.94 (1H,bs); 10.03 (1H,bs).

F.A.B. M.S.: m/z 1005, M$^+$+H; 1027, M$^+$+Na.

U.V. (H$_2$O)nm: λ max (E$_{1cm}$1%): 304 (366), 226 (1002).

8,8'-(carbonyl-bis(imino-N-methyl-4,2-pyrrolecarbonyl-amino(N-methyl-4,2-pyrrole)carbonylimino))bis(1-naphthalensulfonic acid) disodium salt;

8-8'-(carbonyl-bis(imino-N-methyl-4,2-pyrrolecarbonyl-imino(N-methyl-4,2-pyrrole)carbonylimino))bis(5-naphthalensulfonic acid) disodium salt;

8,8'-(carbonyl-bis(imino-N-methyl-4,2-pyrrolecarbonyl-imino(N-methyl-4,2-pyrrole)carbonylimino))-bis(1,3-naphthalendisulfonic acid) tetrasodium salt;

8-8'-(carbonyl-bis(imino-N-methyl-4,2-pyrrolecarbonyl-imino(N-methyl-4,2-pyrrole)carbonylimino))-bis(3,5-naphthalendisulfonic acid) tetrasodium salt;

8,8'-(carbonyl-bis(imino-N-methyl-4,2-pyrrolecarbonyl-imino(N-methyl-4,2-pyrrole)carbonylimino))-bis(2,5-naphthalendisulfonic acid) tetrasodium salt;

8,8'-(carbonyl-bis(imino-N-methyl-4,2-pyrrolecarbonyl-imino(N-methyl-4,2-pyrrole)carbonylimino))-bis(2,4-naphthalendisulfonic acid) tetrasodium salt;

8-8'-(carbonyl-bis(imino-N-methyl-4,2-pyrrolecarbonyl-imino(N-methyl-4,2-pyrrole)carbonylimino))-bis(1,6-naphthalendisulfonic acid) tetrasodium salt;

8,8'-(carbonyl-bis(imino-N-methyl-4,2-pyrrolecarbonyl-imino(N-methyl-4,2-pyrrole)carbonylimino))-bis(2,6-naphthalendisulfonic acid) tetrasodium salt; and 8-8'-(carbonyl-bis(imino-N-methyl-4,2-pyrrolecarbonyl-imino(N-methyl-4,2-pyrrole)carbonylimino))-bis(3,6-naphthalendisulfonic acid) tetrasodium salt.

EXAMPLE 2

8,8'-(carbonyl-bis(imino-N-methyl-4,2-pyrrolecarbonyl-imino(N-methyl-4,2-pyrrole)carbonylimino))-bis(1,3,5-naphthalentrisulfonic acid) hexasodium salt To a solution of 8-(amino-N-methyl-4,2-pyrrolecarbonyl-imino(N-methyl-4,2-pyrrole)carbonylimino))(1,3,5-naphthalentrisulfonic acid trisodium salt) hydrochloride (2.19 g, 3 mmols) in water (60 ml) and dioxane (15 ml), sodium acetate (0.984 g, 12 mmols) was added under stirring. The whole was cooled to 8° C. with an ice bath, then a 20% solution of phosgene in toluene (3 ml, 6 mmols), diluted with ml 9 of dioxane, was added dropwise in 1 hr.

The mixture was stirred 2 hrs at ~8° C.

The solvents were evaporated under vacuum and the residue was taken up with methanol.

After filtration of the salts, the filtrate was evaporated and the residue was cromotographed on a silica gel column with methylene chloride: methanol: water 60:40:4 as eluent, affording g 0.82 of the title compound.

I.R. (KBr)cm$^{-1}$: 3440 b, 1640, 1590, 1190, 1030.

N.M.R. (DMSO-d6): δ 3.80 (3H,s); 3.83 (3H,s); 6.80 (1H,d); 7.06 (2H,m); 7.40 (1H,d); 7.88 (1H,d); 7.99 (1H,d); 8.02 (1H,bs); 8.57 (1H,d); 9.33 (1H,d); 9.91 (1H,bs); 12.29 (1H,bs).

F.A.B.-M.S: m/z 1411, M$^-$-H; 1389, M$^-$-Na.

U.V. (H$_2$O)nm: λ max (E$_1$cm1%): 311 (266), 233 (551).

By analogous procedure the following compounds can be obtained:

8-8'-(carbonyl-bis(imino-N-methyl-4,2-pyrrolecarbonyl-imino(N-methyl-4,2-pyrrole)carbonylimino))-bis(1,4,6-naphthalentrisulonic acid) hexasodium salt;

8,8'-(carbonyl-bis(imino-N-methyl-4,2-pyrrolecarbonyl-imino(N-methyl-4,2-pyrrole)carbonylimino))-bis(2,4,6-naphthalentrisulfonic acid) hexasodium salt;

8,8'-(carbonyl-bis(imino-N-methyl-4,2-pyrrolecarbonyl-imino(N-methyl-4,2-pyrrole)carbonylimino))-bis(1,3,6-naphthalentrisulfonic acid) hexasodium salt; and 8,8'-(carbonyl-bis(imino-N-methyl-4,2-pyrrolecarbonyl-imino(N-methyl-4,2-pyrrole)carbonylimino))-bis(2,3,5-naphthalentrisulfonic acid) hexasodium salt.

EXAMPLE 3

8-(amino-N-methyl-4,2-pyrrolecarbonyl-imino(N-methyl-4,2-pyrrole) carbonylimino))
(1,3,5-naphthalentrisulfonic acid trisodium salt) hydrochloride The compound 8-(nitro-N-methyl-4,2-pyrrolecarbonyl-imino(N-methyl-4,2-pyrrole)carbonylimino))(1,3,5-naphthalentrisulfonic acid trisodium salt) (2.17 g=3 mmols) was dissolved into a mixture of water (120 ml) and 1N HCl (3 ml) and reduced over a Pd catalyst (10% on carbon; mg 900) under $H_2$ pressure (50 p.s.i.) for 3 hours.

The catalyst was filtered and the resulting solution was concentrated in vacuum to dryness, affording 2,1 g of the title compound.

I.R. (KBr) cm$^{-1}$: 3440 b, 1640, 1520, 1190, 1030.

N.M.R. (DMSO-d6): δ 3.85 (3H,s); 3.90 (3H,s); 7.1 (3H,m); 7.4 (1H,d); 7.95 (2H,m); 8.60 (1H,d); 9.35 (1H,d); 10.1 (4H,bs); 12.3 (1H, bs).

EXAMPLE 4

8(nitro-N-methyl-4,2-pyrrolecarbonyl-imino(N-methyl-4,2-pyrrole)carbonylimino))(1,3,5-naphthalenetrisulfonic acic trisodium salt)

To a solution of 8-(amino(N-methyl-4,2-pyrrole)carbonylimino)(1,3,5-naphthalentrisulfonic acid trisodium salt)hydrochloride (1.824 g, 3 mmols) in water (45 ml) and 1N NaOH (1 ml), sodium acetate (0.492 g, 6 mmols) was added under stirring.

The solution was cooled at 5° C. with an ice bath, then a solution of (4-nitro-N methyl-2-pyrrole) carbonyl chloride (0.567 g, 3 mmols) in dioxane (30 ml) was added dropwise in 1 hr. The mixture was stirred 1 hr at 5° C., acidified at pH 4 with 1N HCl and evaporated under vacuum to dryness. The residue was treated with ethyl acetate (300 ml), stirred for 1 hour and filtered, to obtain the title compound (2.1 g).

I.R. (KBr) cm$^{-1}$3440 b, 1650, 1520, 1305, 1195, 1030.

N.M.R. (DMSO-d6; 80 M.Hz.) δ :3.89 (3H, s); 3.99 (3H, s); 7.18 (1H, d); 7.46 (1H, d); 7.70 (1H, d); 8.02 (2H, m); 8.2 (1H, d); 8.63 (1H, d); 9.41 (1H, d); 10.45 (1H, b s); 12.42 (1H, b s).

EXAMPLE 5

8-(amino(N-methyl-4,2-pyrrole)carbonylimino)(1,3,5-naphthalentrisulfonic acid trisodium salt), hydrochloride The solution of 8-(nitro(N methyl-4,2-pyrrole)carbonylimino) (1,3,5-naphthalentrisulfonic acid trisodium salt) (1.803 g=3 mmols) in water (120 ml) and 1NHCl (3 ml) was reduced over a Pd catalyst (10% on carbon g 800) under $H_2$ pressure (50 p.s.i.) for 4 h.

The catalyst was filtered and the resulting solution was concentrated in vacuum to dryness, affording 1.8 g of the title compound.

I.R. (KBr) cm$^{-1}$: 3440 b, 1640, 1520, 1190, 1030.

N.M.R. (DMSO-d6): δ 3.9 (3H, s); 7.11 (1H, d); 7.29 (1H, d); 8.04 (2H, m); 8.6 (1H, d); 9.88 (1H, d); 10.04 (3H, b s); 12.39 (1H, b s).

EXAMPLE 6

8-(nitro(N-methyl-4.2-pyrrole) carbonylimino)(1,3,5-naphthalentrisulfonic acid trisodium salt)

To a solution of 8-amino, 1,3,5-naphthalentrisulfonic acid trisodium salt (1.347 g=3 mmols) in water (45 ml), sodium acetate (0.492 g=6 mM) was added under stirring. The solution was cooled at 5° C. with an ice bath, then a solution of (4-nitro-N methyl-2-pyrrole)carbonyl chloride (0.943=5 mmols) in dioxane (45 ml) was added dropwise in 1 h. The mixture was stirred 3 h at 5° C., acidified and pH 4 with 1N HCl and evaporated under vacuum to dryness.

The residue was treated with ethylacetate (300 ml), stirred for 1 hour and filtered, to obtain g 1.7 of the title compound.

I.R. (KBr) cm$^{-1}$: 3440 b, 1650, 1530, 1305, 1200, 1030.

N.M.R. (DMSO-d6): δ 3.96 (3H,s); 7.84 (1H,d); 8.06 (2H,m); 8.15 (1H,d); 8.63 (1H,d); 9.4 (1H,d); 12.55 (1H, bs).

EXAMPLE 7

7,7'-(carbonyl-bis(imino-N-methyl-4.2-pyrrole)carbonylimino))(N-methyl-4.2-pyrrole)carbonylimino))-bis(1.3-naphthalendisulfonic acid) tetrapotassium salt.

To a solution of 7-(amino-N-methyl-4.2-pyrrolecarbonylimino(N-methyl-4,2-pyrrole)carbonylimino))(1,3-naphthalendisulfonic acid dipotassium salt) hydrochloride (160 mg, 0.24 mmols) in water (15 ml) and dioxane (10 ml), potassium acetate (50 mg, 0.51 mmols) was added under stirring. A 20% solution of phosgene in toluene (0.5 ml, ≃ 1 mmol), diluted with dioxane (2 ml), was added dropwise in half hr at room temperature. The mixture was stirred 1 hr. at room temperature.

The solvents were evaporated undervacuum, the residue was cromatographed on a silica gel column with methylene chloride:methanol:water 40:60:6 as eluent, affording 90 mg of the title compound.

I.R. (KBr) cm$^{-1}$: 3450 (b); 1650; 1580; 1530; 1190; 1030.

N.M.R. (DMSO-d6): δ 3.84 (3H,s); 3.87 (3H,s); 6.80 (1H,d); 7.05 (1H,d); 7.18 (1H,d); 7.33 (1H,d); 7.86 (2H,m); 8.00 (1H,d); 8.16 (1H,bs); 8.21 (1H,d); 8.95 (1H,bs); 9.86 (1H, bs); 10.21 (1H, bs).

U.V. ($H_2O$)mm: λ max ($E_1$ $_{cm}$$^1$%): 316.8 (371), 248.95 (444).

F.A.B. M.J.: m/z: 1273 (M$^+$+H); 1311 (M$^+$+K).

By analogous procedure the following compounds can be obtained:

7,7'-(carbonyl-bis(imino-N-methyl-4,2-pyrrolecarbonyl-imino(N-methyl-4,2-pyrrole)carbonylimino))-bis(1-naphthalensulfonic acid) disodium salt;

7,7'-(carbonyl-bis(imino-N-methyl-4,2-pyrrolecarbonyl-imino(N-methyl-4,2-pyrrole)carbonylimino))-bis(2-naphthalensulfonic acid) disodium salt;

7,7'-(carbonyl-bis(imino-N-methyl-4,2-pyrrole-carbonyl-imino(N-methyl-4,2-pyrrole)carbonylimino))-bis(3-naphthalensulfonic acid) disodium salt;

7,7'-(carbonyl-bis(imino-N-methyl-4,2-pyrrolecarbonyl-imino(N-methyl-4,2-pyrrole)carbonylimino))-bis(4-naphthalensulfonic acid) disodium salt;

7,7'-(carbonyl-bis(imino-N-methyl-4,2-pyrrolecarbonyl-imino(N-methyl-4,2-pyrrole)carbonylimino))-bis(2,3-naphthalendisulfonic acid) tetrasodium salt;

7,7'-(carbonyl-bis(imino-N-methyl-4,2-pyrrolecarbo-
nyl-imino(N-methyl-4,2-pyrrole)carbonylimino))-
bis(2,4-naphthalendisulfonic acid) tetrasodium salt;
7,7'-(carbonyl-bis(imino-N-methyl-4,2-pyrrolecarbo-
nyl-imino(N-methyl-4,2-pyrrole)carbonylimino))-
bis(1,5-naphthalendisulfonic acid) tetrasodium salt;
7,7'-(carbonly-bis(imino-N-methyl-4,2-pyrrolecarbo-
nyl-imino(N-methyl-4,2-pyrrole)carbonylimino))-
bis(2,5-naphthalendisulfonic acid) tetrasodium salt;
7,7'-(carbonyl-bis(imino-N-methyl-4,2-pyrrolecarbony-
imino(N-methyl-4,2-pyrrole)carbonylimino))bis(3,5-
naphthalendisulfonic salt;
7,7'-(carbonyl-bis(imino-N-methyl-4,2-pyrrolecarbo-
nyl-imino(N-methyl-4,2-pyrrole)carbonylimino))-
bis(1,6-naphthalendisulfonic acid) tetrasodium salt;
7,7'-(carbonyl-bis(imino-N-methyl-4,2-pyrrlecarbonyl-
imino(N-methyl-4,2-pyrrole)carbonylimino))bis(2,6-
naphthamendisulfonic acid) tetrasodium salt;
7,7'-(carbonyl-bis(imino-N-methyl-4,2-pyrrolecarbo-
nyl-imino(N-methyl-4,2-pyrrole)carbonylimino))-
bis(3,6-naphthalendisulfonic acid) tetrasodium salt;
7-7'-(carbonyl-bis(imino-N-methyl-4,2-pyrrolecarbo-
nyl-imino(N-methyl-4,2-pyrrole)carbonylimino))-
bis(1,3,5-naphthalentrisulfonic acid) hexasodium salt;
7,7'-(carbonyl-bis(imino-N-methyl-4,2-pyrrolecarbo-
nyl-imino(N-methyl-4,2-pyrrole)carbonylimino))-
bis(1,4,6-naphthalentrisulfonic acid) hexasodium salt;
7,7'-(carbonyl-bis(imino-N-methyl-4,2-pyrrolecarbo-
nyl-imino(N-methyl-4,2-pyrrole)carbonylimino))-
bis(1,3,6-naphthalentrisulfonic acid) bexasodium salt;
7,7'-(carbonyl-bis(imino-N-methyl-4,2-pyrrole-carbo-
nyl-imino(N-methyl-4,2-pyrrole)carbonylimino))-
bis(2,4,6-naphthalentrisulfonic acid) hexasodium salt;
7,7'-(carbonyl-bis(imino-N-methyl-4,2-pyrrolecarbo-
nyl-imino(N-methyl-4,21-pyrrole)carbonylimino))-
bis(2,3,5-naphthalentrisulfonic acid) hexasodium salt;
2,2'-(carbonyl-bis(imino-N-methyl-4,2-pyrrolecarbo-
nyl-imino(N-methyl-4,2-pyrrole)carbonylimino))-
bis(2-deoxy-D-glucose-6-sulfate) disodium salt;
2,2'-(carbonyl-bis(imino-N-methyl-4,2-pyrrolecarbo-
nyl-imino(N-methyl-4,2-pyrrole)carbonylimino))-
bis(2-deoxy-D-glucose-6-phosphate) disodium salt;
5,5'-(carbonyl-bis(imino-N-methyl-4,2-pyrrocarbonyl-
imino(N-methyl-4,2-pyrrole)carbonylimino))bis(8-
quinolinesulfonic acid) disodium salt;
5,5'-(carbonyl-bis(imino-N-methyl-4,2-pyrrolecarbo-
nyl-imino(N-methyl-4,2-pyrrole)carbonylimino))-
bis(6-quinolinesulfonic acid) disodium salt;
8,8'-(carbonyl-bis(imino-N-methyl-4,2-pyrrolcarbonyl-
imino(N-methyl-4,2-pyrrole)carbonylimino))bis(5,7-
quinolinedisulfonic acid) tetrasodium salt; and
5,5'-(carbonyl-bis(imino-N-methyl-4,2-pyrrolecarbo-
nyl-imino(N-methyl-4,2-pyrrole)carbonylimino))-
bis(6,8-quinolinedisulfonic acid) tetrasodium salt.

EXAMPLE 8

8,8'-carbonyl-bis(imino-N-methyl-4,2-pyrrolecarbonyl-
imino(N-methyl-4,2-pyrrole)carbonylimino))bis(1,3,5-
naphthanentrisulfonic Acid)

A solution of 8,8'-(carbonyl-bis(imino-N-methyl-4,2-pyrrolecarbonyl-imino(N-methyl-4,2-pyrrole)carbonylimino))bis(1,3,5-naphthalentrisulfonic acid) hexasodium salt (400 mg) in water (10 ml), is chromatographed on an Amberlite 1R-120(H) column (20 ml), with water as eluent.

The solution is evaporated to dryness in vacuum, affording 0,3 g of the title compound.

EXAMPLE 9

Intramuscular Injection 40 Mg/Ml.

A injectable pharmaceutical preparation can be manufactured by dissolving 40 g of 8,8'-(carbonyl-bis(imino-N-methyl-4,2-pyrrole-carbonyl-imino(N-methyl-4,2-pyrrole)carbonylimino))bis(1,3,5-naphthalentrisulfonic acid) hexasodium salt in water for injection (1000 ml) and sealing ampoules of 1-10 ml.

We claim:

1. A compound of formula (II)

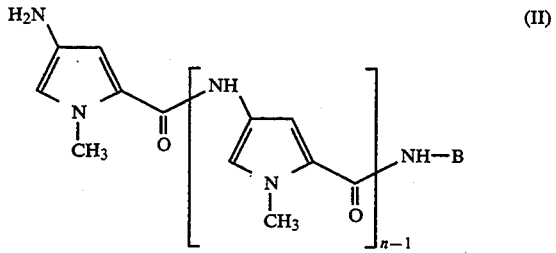

wherein n is an integer of 1 to 3 and B is a member selected from the group consisting of a phenyl group, a naphthyl group, a tetrahydropyranyl ring, a tetrahydrofuranyl ring, a quinoline ring, a pyranyl sugar residue and a furanyl sugar residue, wherein said member is substituted by 1 to 3 acid groups independently selected from the group consisting of sulfonic, sulfuric, sulfamic, sulfinic, phosphoric, phosphonic, phosphamic and carboxylic acid groups; or a salt thereof.

2. A compound according to claim 1, selected from the group consisting of:
8-(amino-N-methyl-4,2-pyrrolecarbonyl-imino(N-methyl-4,2-pyrrole)carbonylimino) (1,5-naphthalendisulfonic acid disodium salt)hydrochloride;
8-(amino-N-methyl-4,2-pyrrolecarbonyl-imino(N-methyl-4,2-pyrrole)carbonylimino) (1,3,5-naphthalentrisulfonic acid trisodium salt)hydrochloride;
8-(amino(N-methyl-4,2-pyrrole)carbonylimino) (1,3,5-naphthalentrisulfonic acid trisodium salt)hydrochloride; and
7-(amino-N-methyl-4,2-pyrrolecarbonylimino(N-methyl-4,2-pyrrole)carbonylimino) (1,3-naphthalendisulfonic acid dipotassium salt)hydrochloride.

* * * * *